US00PP12461P2

(12) United States Plant Patent
Akerboom

(10) Patent No.: US PP12,461 P2
(45) Date of Patent: Mar. 12, 2002

(54) ASTER PLANT NAMED 'PINK MILKA'

(75) Inventor: Petrus J. Akerboom, Ter Aar (NL)

(73) Assignee: De Nachtvlinder B.V., Ter Aar (NL)

( * ) Notice: Subject to any disclaimer, the term of this patent is extended or adjusted under 35 U.S.C. 154(b) by 0 days.

(21) Appl. No.: 09/263,152

(22) Filed: Mar. 5, 1999

(51) Int. Cl.[7] ..... A01H 5/00
(52) U.S. Cl. ..... Plt./355
(58) Field of Search ..... Plt./355

(56) References Cited

U.S. PATENT DOCUMENTS

PP10,602 P * 9/1998 Akerboom ..... Plt./355

OTHER PUBLICATIONS

UPOV–ROM GTITM Computer Database 2000/02, GTI JOUVE Retrieval Software, citations for 'Pink Milka', May 2000.*
UPOV–ROM GTITM Computer Database 2000/04, GTI JOUVE retrieval software, citations for 'Pink Milka', Aug. 2000.*

* cited by examiner

*Primary Examiner*—Bruce R. Campell
*Assistant Examiner*—Wendy A Baker
(74) *Attorney, Agent, or Firm*—C. A. Whealy

(57) ABSTRACT

A distinct cultivar of Aster plant named 'Pink Milka', characterized by its freely and uniform flowering; decorative inflorescence form with light pink ray florets; and good post-production longevity.

1 Drawing Sheet

BACKGROUND OF THE INVENTION

The present Invention relates to a new and distinct cultivar of Aster plant, botanically known as *Aster novi-belgii* and referred to by the cultivar name Pink Milka.

The new Aster is a whole plant mutation of the commercial *Aster novi-belgii* cultivar Milka, disclosed in U.S. Plant Pat. No. 10,602. The new Aster was discovered and selected by the Inventor in a controlled environment in Ter Aar, The Netherlands, as a single flowering plant among a population of plants of the parent cultivar Milka in June, 1994. This single plant consistently formed inflorescences having light pink ray florets compared to the light purple ray florets of the cultivar Milka.

Asexual reproduction of the new Aster by terminal cuttings taken at Ter Aar, The Netherlands, has shown that the unique features of this new Aster are stable and reproduced true to type in successive generations.

SUMMARY OF THE INVENTION

The following traits have been repeatedly observed and are determined to be the unique characteristics of 'Pink Milka'. These characteristics in combination distinguish 'Pink Milka' as a new and distinct cultivar:

1. Freely and uniform flowering.

2. Decorative inflorescence form with light pink ray florets.

3. Good post-production longevity.

Plants of the new Aster can be compared to plants of the sibling cultivar Dark Milka (U.S. Plant patent application Ser. No. 09/263,154). Plants of the new Aster have narrowly obovate and light pink ray florets whereas plants of the cultivar Dark Milka have narrowly elliptic and dark purple ray florets.

Plants of the new Aster can also be compared to plants of the sibling cultivar Karmijn Milka (U.S. Plant patent application Ser. No. 09/263,153). Plants of the new Aster have narrowly obovate and light pink ray florets whereas plants of the cultivar Karmijn Milka have narrowly elliptic and purple ray florets.

The cultivar Pink Milka has not been observed under all possible environmental conditions. The phenotype may vary somewhat with variations in environment such as temperature, daylength and light intensity, without, however, any variance in genotype.

BRIEF DESCRIPTION OF THE PHOTOGRAPH

The accompanying colored photograph illustrates the overall appearance of the new Aster, showing the colors as true as it is reasonably possible to obtain in colored reproductions of this type. Colors in the photograph may differ slightly from the color values cited in the detailed botanical description which accurately describe the colors of the new Aster. The photograph comprises a side perspective view of a typical cut flower stem of the new Aster.

DETAILED BOTANICAL DESCRIPTION

In the following description, color references are made to The Royal Horticultural Society Colour Chart except where general terms of ordinary dictionary significance are used. The following observations and measurements describe plants grown as cut flowers during the summer in Ter Aar, The Netherlands, in a glass-covered greenhouse with average day temperatures of 17 to 35° C. and night temperatures of 14 to 20° C. Plants received long day/short night treatments, 18 hours light, for seven weeks and then were forced into flower with short day/long night treatments, 12 hours light.

Botanical classification: *Aster novi-belgii* cultivar Pink Milka.

Commercial classification: Cut flower Aster; can also be produced as a potted plant.

Parentage: Whole plant mutation of *Aster novi-belgii* cultivar Milka, disclosed in U.S. Plant Pat. No. 10,602.

Propagation:

*Type.*—Terminal tip cuttings.

*Time to initiate roots.*—About 8 to 10 days at a temperature of 18 to 23° C.

*Time to develop roots.*—Summer: About 16 to 20 days at a temperature of 23° C. Winter: About 20 to 25 days at a temperature of 18° C.

*Root description.*—Fine, fibrous and well-branched.

Plant description:

*Appearance.*—Herbaceous cut flower. Stems upright; medium plant height at flowering. Freely and uniformly flowering; light pink-colored decorative inflorescences.

*Crop time.*—About 12.5 to 13 weeks from planting to harvest of cut flowering stems.

*Branching habit.*—Freely branching, typically more than 25 lateral branches per plant.

*Growth rate.*—Moderate to slow.

*Plant height.*—About 100 to 110 cm.

*Plant width.*—About 35 cm.

*Lateral branch length.*—At the top of the flowering stem: About 1 mm. At the middle of the flowering stem: About 18 to 30 cm. At the bottom of the flowering stem: About 2 to 13 cm.

*Lateral branch diameter.*—At the top of the flowering stem: About 1.1 mm. At the middle of the flowering stem: About 1.5 to 1.8 mm. At the bottom of the flowering stem: About 2 to 2.3 mm.

*Internode length.*—$5^{th}$ node from apex: About 1.6 to 1.8 cm. $10^{th}$ node from apex: About 1.8 to 2.5 cm. $15^{th}$ node from apex: About 2.1 to 2.6 cm. $20^{th}$ node from apex: About 2.2 to 3.1 cm.

*Stem color.*—Green, 144A to 146A, no anthocyanin at internodes.

*Stem texture.*—Moderately pubescent.

*Foliage description.*—Arrangement: Alternate. Quantity: About 38 to 45 per lateral stem. Shape: Linear; apex acute; base attenuate, sessile; margin serrate. Size: At the top of the flowering stem: About 1 to 1.7 cm in length and about 1.8 to 2.6 mm in width. At the middle of the flowering stem: About 13.7 to 15.4 cm in length and about 1.3 to 1.7 cm in width. At the bottom of the flowering stem: About 17.8 to 19.4 cm in length and about 2 to 2.5 in width. Texture: Glabrous, leathery. Color: Young leaves, upper surface: 147A. Young leaves, lower surface: Slightly lighter than 137C. Fully expanded leaves, upper surface: 147A. Fully expanded leaves, lower surface: 146B. Venation, upper and lower surfaces: 145C.

Flowering description:

*Appearance.*—Decorative inflorescence form. Inflorescences held on wiry peduncles, arising from leaf axils; inflorescences face upright. Disc and ray florets arranged acropetally on a capitulum.

*Flowering response.*—Under natural conditions, plants flower in the late summer/autumn. At other times of the year, inflorescence initiation and development can be induced under short day/long night conditions. Response time is about 5.5 to 6 weeks.

*Post-production longevity.*—Good, inflorescences last about 3.5 to 4.5 weeks on the plant; about 2 to 3 weeks as a cut flower without postproduction treatments. Inflorescences persistent.

*Quantity of inflorescences.*—Inflorescences form at every leaf axil. Freely flowering, usually about 52 to 78 inflorescences per flowering stem.

*Fragrance.*—None.

*Inflorescence size.*—Diameter: About 3.3 cm. Depth (height): About 1 to 1.4 cm. Disc diameter: About 7.5 mm.

*Inflorescence bud.*—Shape: Cylindrical. Length: About 7 to 8 mm. Diameter: About 7 to 8 mm. Color: 137B.

*Ray florets.*—Quantity of ray florets per inflorescence: About 132 to 145. Shape: Narrowly obovate; apex rounded; base attenuate; margin entire. Length: About 1.1 to 1.3 cm. Width: About 1.3 to 2 mm. Texture: Satiny, smooth and glabrous. Color: When opening, upper surface: 75C. When opening, lower surface: 75D. Mature, upper surface: 77B to 75A; fading to 75B to 75D. Mature, lower surface: 75D.

*Disc florets.*—Quantity: About 137 per inflorescence. Shape: Tubular. Length: About 7 mm. Diameter: At apex, about 2 mm; at base, about 1 mm. Color: Immature: 145A to 154A. Mature: 9A.

*Peduncle.*—Strength: Strong. Length: Apical peduncle: About 4 to 6 mm. Fourth peduncle: About 2 to 3 mm. Seventh peduncle: About 2 mm. Color: 146A to 147A.

*Reproductive organs.*—Androecium: Not present on ray florets. Gynoecium: Pistil length: About 3.5 to 4.5 mm. Stigma color: Yellow, 10D. Style length: About 2 mm.

*Seed development.*—Not observed.

Disease resistance: Plants of the new Aster have not been observed to be resistant to pathogens common to Asters, however plants of the new Aster appear to be less sensitive to Powdery Mildew than other known cultivars of Aster.

It is claimed:

1. A new and distinct cultivar of Aster plant named 'Pink Milka', as illustrated and described.

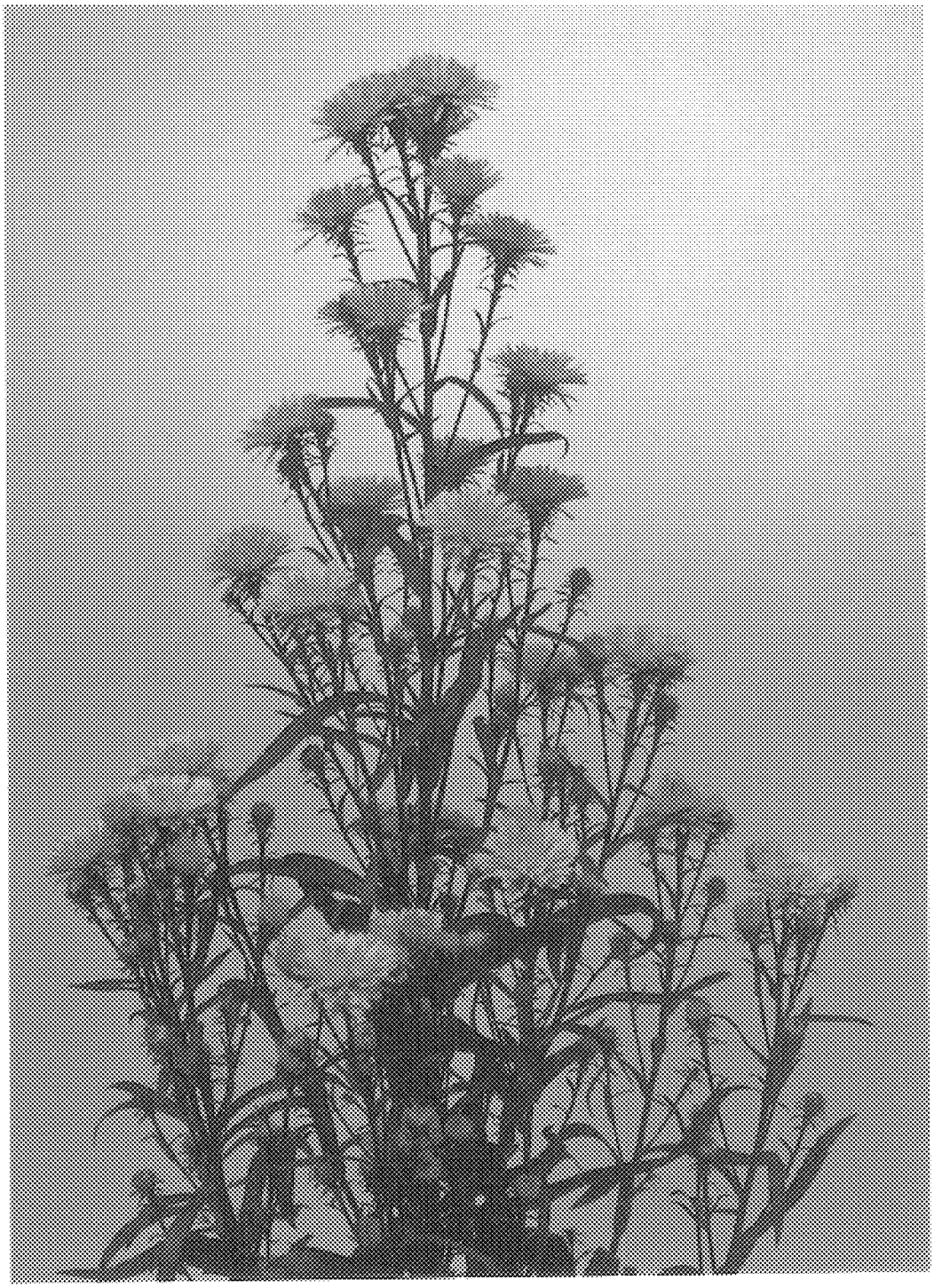

* * * * *